US012600067B2

(12) United States Patent
Kubo

(10) Patent No.: US 12,600,067 B2
(45) Date of Patent: *Apr. 14, 2026

(54) INJECTION DEVICE

(71) Applicant: Sodick Co., Ltd., Kanagawa (JP)

(72) Inventor: Yoshikazu Kubo, Kanagawa (JP)

(73) Assignee: Sodick Co., Ltd., Kanagawa (JP)

( * ) Notice: Subject to any disclaimer, the term of this patent is extended or adjusted under 35 U.S.C. 154(b) by 61 days.

This patent is subject to a terminal disclaimer.

(21) Appl. No.: 18/919,462

(22) Filed: Oct. 18, 2024

(65) Prior Publication Data

US 2025/0042072 A1     Feb. 6, 2025

Related U.S. Application Data

(62) Division of application No. 17/080,865, filed on Oct. 27, 2020, now Pat. No. 12,162,196.

(30) Foreign Application Priority Data

Nov. 11, 2019 (JP) ................................. 2019-203819
Jun. 16, 2020 (JP) ................................. 2020-103847
Jun. 16, 2020 (JP) ................................. 2020-103848

(51) Int. Cl.
| | |
|---|---|
| B29C 45/17 | (2006.01) |
| A61M 5/315 | (2006.01) |
| B29C 45/18 | (2006.01) |
| B29C 45/40 | (2006.01) |
| B29C 45/50 | (2006.01) |
| B29C 45/53 | (2006.01) |
| B29C 45/58 | (2006.01) |
| B29C 45/74 | (2006.01) |
| B29C 45/77 | (2006.01) |

(52) U.S. Cl.
CPC ..... *B29C 45/1704* (2013.01); *A61M 5/31501* (2013.01); *B29C 45/1816* (2013.01); *B29C 45/401* (2013.01); *B29C 45/5008* (2013.01); *B29C 45/53* (2013.01); *B29C 45/586* (2013.01); *B29C 45/74* (2013.01); *B29C 45/77* (2013.01)

(58) Field of Classification Search
None
See application file for complete search history.

(56) References Cited

U.S. PATENT DOCUMENTS

| | | | | |
|---|---|---|---|---|
| 5,785,999 A * | 7/1998 | Takayama | ........... | B29C 45/1735 264/572 |
| 7,318,713 B2 * | 1/2008 | Xu | ........................ | B29C 48/575 425/208 |
| 2020/0269535 A1 * | 8/2020 | Falken | ............... | B29D 35/0009 |

* cited by examiner

*Primary Examiner* — Armand Melendez
(74) *Attorney, Agent, or Firm* — JCIPRNET

(57) ABSTRACT

After the injection shaft moves backward and the gas is supplied into the injection chamber, it is desired to accurately control the gas supply amount in the injection device in which the injection shaft is moved forward to compress and dissolve the gas in the molding material in the injection chamber. An injection device of the disclosure supplies a gas into an injection chamber via a gas supply hole which passes through an injection shaft and is opened at a tip surface of the injection shaft. The injection device of the disclosure has at least one seal ring and at least one piston ring aligned in an axial direction on an outer circumferential surface of the injection shaft.

20 Claims, 10 Drawing Sheets

31b  31  30  31a 31b  31  30  31a

INJECTION DEVICE

CROSS-REFERENCE TO RELATED APPLICATION

This is a divisional application of patent application Ser. No. 17/080,865, filed on Oct. 27, 2020, which claims the priority benefit of Japan application serial no. 2019-203819, filed on Nov. 11, 2019, Japan application serial no. 2020-103847, filed on Jun. 16, 2020, and Japan application serial no. 2020-103848, filed on Jun. 16, 2020. The entirety of each of the above-mentioned patent applications is hereby incorporated by reference herein and made a part of this specification.

BACKGROUND

Technical Field

The disclosure relates to an injection device of an injection molding machine which injects a molding material in which a gas is compressed and dissolved to obtain a molded product.

Related Art

As an injection device provided in an injection molding machine, as disclosed in, for example, Patent Document 1 (Japanese Patent Application Laid-Open No. 3-97518), Patent Document 2 (Japanese Patent Publication No. 2615334), and Patent Document 3 (US 2018-0133940 A1), a so-called preplasticizing injection device is conventionally known to be separately provided with a plasticization part for plasticizing a thermoplastic molding material by a plasticization screw, and an injection part for pushing and injecting a molten molding material plasticized by the plasticization part into a mold by an injection shaft. In addition, as disclosed in Patent Document 3, for example, a preplasticizing injection device is also known to be separately provided with a mixing part for mixing a thermosetting molding material and an additive by a mixing shaft, and an injection part for pushing and injecting a liquid molding material mixed by the mixing part into a mold by an injection shaft. Moreover, for example, a preplasticizing injection device is also known to be separately provided with a mixing part for mixing a thermosetting molding material and an additive by a static mixer, and an injection part for pushing and injecting a liquid molding material mixed by the mixing part into a mold by an injection shaft. For example, an injection plunger or an injection screw is used as the injection shaft.

As another injection device, an in-line screw injection device is conventionally known to perform both plasticization and injection with one injection shaft. Further, an in-line screw injection device is also known to perform both mixing and injection with one injection shaft. For example, an in-line screw is used as the injection shaft.

Regarding the injection control of a general injection part, in an injection process, the moving speed of the injection shaft is preferentially controlled, and the injection shaft is greatly moved forward to inject the molding material into the mold; afterwards, in a pressure holding process, the pressure applied to the injection shaft is preferentially controlled to replenish the amount of the molding material cooling and shrinking in the mold.

On the other hand, as shown in, for example, Patent Document 4 (Japanese Patent Publication No. 4148583), when the resin to be molded by an injection molding method is a resin having high viscosity and difficult to mold, it is known that a gas is dissolved in the difficult-to-mold resin under high pressure to reduce the viscosity of the difficult-to-mold resin. Moreover, as a method of dissolving the gas in the difficult-to-mold resin, Patent Document 4 discloses a method of directly supplying a gas from a gas cylinder to the difficult-to-mold resin, and a method of pressurized supply by using a plunger pump or the like.

However, according to the study by the inventors of the disclosure, in an injection part of a conventional injection device, if moving an injection shaft backward and forward in an injection chamber accommodating a molding material is applied as a means for compressing and dissolving a gas supplied into the injection chamber in the molding material in the injection chamber, it has been found that it may be difficult to accurately control the gas supply amount. The disclosure has been made in view of the above circumstances, and it is an objective of the disclosure to provide an injection device capable of compressing and dissolving a gas in a molding material by an injection shaft while controlling the supply amount accurately in the injection device.

SUMMARY

An injection device of the disclosure injects a molding material into a mold. The injection device includes an injection cylinder, a supply device, a gas supply device, a gas integrated flow measuring device, an injection shaft, an injection driving device, and an injection control device. The injection cylinder is formed with an injection chamber accommodating the molding material. The supply device supplies the molding material into the injection chamber. The gas supply device supplies a gas into the injection chamber to compress and dissolve the gas in the molding material supplied into the injection chamber. The gas integrated flow measuring device measures an integrated flow of the gas supplied into the injection chamber. The injection shaft reciprocates in a cylinder axis direction in the injection chamber and is formed with a gas supply hole penetrating inside the injection shaft. One end part of the gas supply hole is opened on a tip surface forming a part of a wall surface of the injection chamber, and another end part of the gas supply hole is connected to the gas supply device to guide the gas from the gas supply device into the injection chamber. The injection driving device causes the injection shaft to reciprocate in the cylinder axis direction. The injection control device controls the injection driving device to move the injection shaft backward and forward in the injection chamber to expand and reduce the injection chamber before supplying the molding material from the supply device into the injection chamber. When compressing and dissolving a predetermined amount of the gas in the molding material remaining in the injection chamber, a cycle from moving the injection shaft backward to supply the gas into the injection chamber to moving the injection shaft forward to compress and dissolve the gas in the injection chamber into the molding material in the injection chamber is performed for at least one time until the integrated flow measured by the gas integrated flow measuring device reaches the predetermined amount. The injection control device stops backward movement of the injection shaft and moves the injection shaft forward to an initial position when the integrated flow measured by the gas integrated flow measuring device reaches the predetermined amount. Then, as the injection shaft is pushed back by the molding material supplied into the injection chamber from the supply device, stop the injection shaft at a position where an amount of the molding material in the injection chamber reaches a predetermined amount, thereafter move the injection shaft forward at a predetermined speed for a predetermined distance to inject the molding material into the mold, and thereafter to perform a pressure holding process in which the injection driving device moves the injection shaft forward at the predetermined pressure for a predetermined time, wherein the initial position is a position at a time when a previous pressure holding process was completed.

An injection device of the disclosure injects a molding material into a mold. The injection device includes an injection cylinder, a supply device, a gas supply device, a gas integrated flow measuring device, an injection shaft, an injection driving device, and an injection control device. The injection cylinder is formed with an injection chamber accommodating the molding material. The supply device supplies the molding material into the injection chamber. The gas supply device supplies a gas into the injection chamber to compress and dissolve the gas in the molding material supplied into the injection chamber. The gas integrated flow measuring device measures an integrated flow of the gas supplied into the injection chamber. The injection shaft reciprocates in a cylinder axis direction in the injection chamber. The injection driving device causes the injection shaft to reciprocate in the cylinder axis direction. The injection control device controls the injection driving device to move the injection shaft backward and forward in the injection chamber to expand and reduce the injection chamber before supplying the molding material from the supply device into the injection chamber. When compressing and dissolving a predetermined amount of the gas in the molding material remaining in the injection chamber, a cycle from moving the injection shaft backward to supply the gas into the injection chamber to moving the injection shaft forward to compress and dissolve the gas in the injection chamber into the molding material in the injection chamber is performed for at least one time until the integrated flow measured by the gas integrated flow measuring device reaches the predetermined amount. The injection control device stops backward movement of the injection shaft and moves the injection shaft forward to an initial position when the integrated flow measured by the gas integrated flow measuring device reaches the predetermined amount. Then, as the injection shaft is pushed back by the molding material supplied into the injection chamber from the supply device, stop the injection shaft at a position where an amount of the molding material in the injection chamber reaches a predetermined amount, thereafter move the injection shaft forward at a predetermined speed for a predetermined distance to inject the molding material into the mold, and thereafter to perform a pressure holding process in which the injection driving device moves the injection shaft forward at the predetermined pressure for a predetermined time, wherein the initial position is a position at a time when a previous pressure holding process was completed.

According to the injection device of the disclosure, it is possible to correctly control the gas supply amount. The detailed reason will be described below in accordance with the embodiment.

DESCRIPTION OF THE EMBODIMENTS

Figure 1:
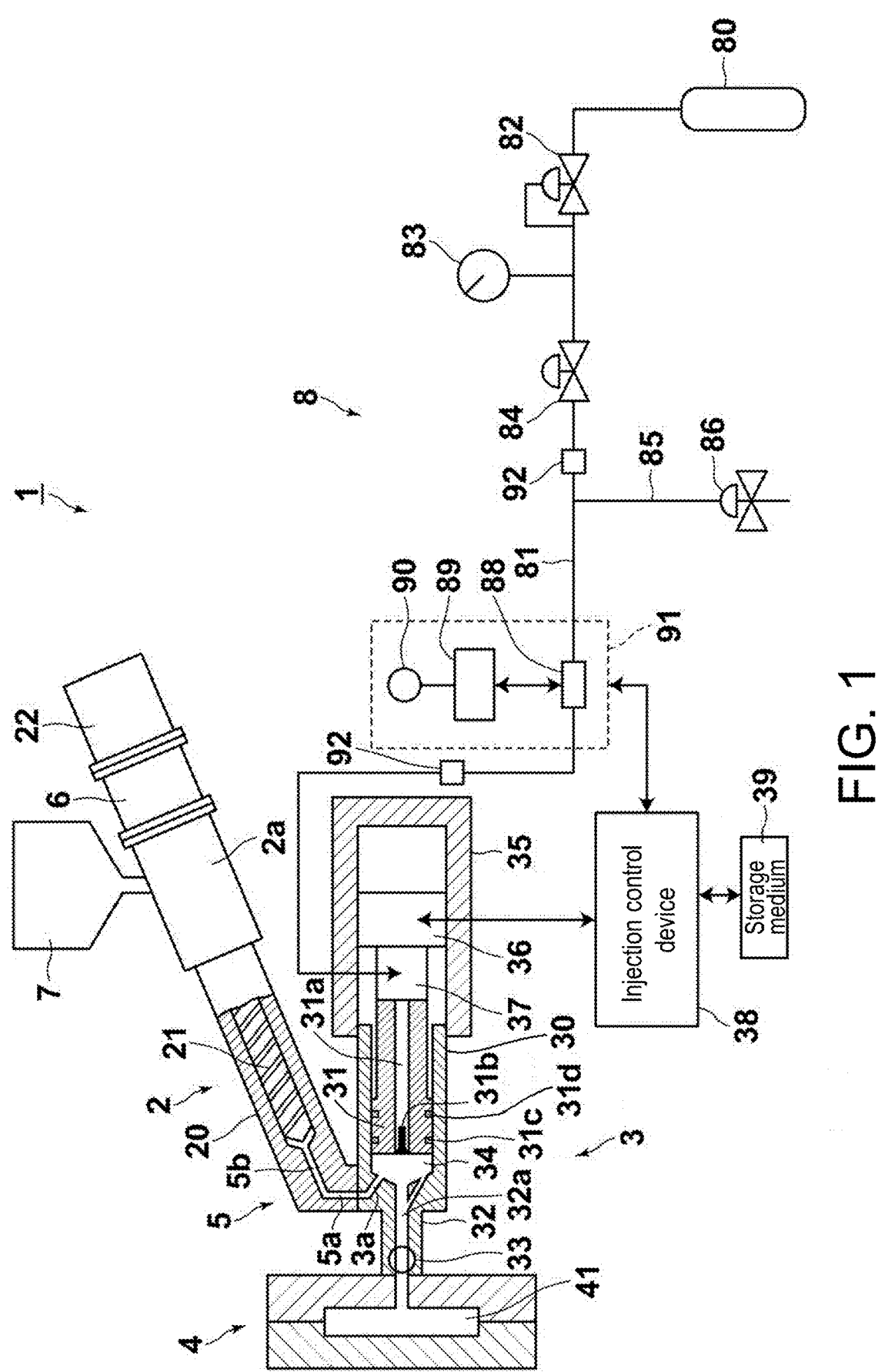
FIG. 1 is a view showing a schematic configuration of a gas injection device in a preplasticizing injection device according to an embodiment of the disclosure.

Hereinafter, an embodiment of the disclosure will be described with reference to the drawings by taking a preplasticizing injection device using a thermoplastic resin as a molding material as an example. FIG. 1 is a view showing a schematic configuration of a preplasticizing injection device 1 (hereinafter simply referred to as "injection device 1") according to an embodiment of the disclosure. The injection device 1 includes a plasticization part 2 which plasticizes a molding material, an injection part 3 which injects a plasticized molding material in a molten state (hereinafter simply referred to as "molding material") supplied from the plasticization part 2 into a cavity space 41 of a mold 4, communication passages 3a and 5a which communicate with the internal spaces of the plasticization part 2 and the injection part 3, and a gas supply device 8. The plasticization part 2 and the injection part 3 are connected by a connection member 5. The connection member 5 is formed with the communication passage 5*a*. An injection molding machine includes at least the injection device 1, a mold clamping device (not shown) which mounts the mold 4, and a controlling device (not shown) which controls these devices. The injection device 1 and the mold clamping device are disposed on a machine base (not shown). In the following description, the case where a thermoplastic resin is used as the molding material will be described as an example. In addition to the thermoplastic resin, the molding material may also be a thermosetting resin, a composite material of such resins and metal, or the like, and is not particularly limited. The plasticization part 2 is a supply device which supplies the molding material to the injection part 3. In the following description, the case where the plasticization part 2 is adopted as the supply device will be described as an example. In addition to the plasticization part 2, if the molding material is a thermosetting resin, for example, the supply device may also be a mixing part or the like which, after mixing the thermosetting resin and an additive, supplies the thermosetting resin mixed with the additive to the injection part 3, and the disclosure is not particularly limited. Also, the supply device may also be a device which simply supplies the molding material to the injection part 3.

The plasticization part 2 includes a plasticization cylinder 20, a plasticization screw 21 disposed inside the plasticization cylinder 20, a rotation driving device 22 which rotates the plasticization screw 21, and a backflow prevention mechanism 6. Further, a hopper 7 for supplying a resin material from the rear end side of the plasticization cylinder 20 is provided. The hopper 7, the plasticization cylinder 20, and the backflow prevention mechanism 6 are attached to a hopper attachment member 2*a*. The rotation driving device 22 is attached to the backflow prevention mechanism 6. A material discharge port of the hopper 7 and a material supply port of the plasticization cylinder 20 communicate with each other inside the hopper attachment member 2*a*. The plasticization cylinder 20 is heated to the inside of the cylinder by, for example, a heater wound around the outer circumference. The mixing part of the preplasticizing injection device using a thermosetting resin material as the molding material includes, for example, a mixing shaft and a mixing cylinder which accommodates the mixing shaft. The mixing cylinder may be cooled by a pipe wound around the outer circumference through which a cooling medium flows.

The inside of the plasticization cylinder 20 is in communication with an injection chamber 34 of the injection part 3 via the communication passage 5*a* of the connection member 5 and the communication passage 3*a* of the injection part 3. A plasticization part side opening 5*b* of the communication passage 5*a* is located on the axial line of the plasticization screw 21. The tip of the plasticization screw 21 is formed in a sharp cone shape. When the rotation driving device 22 is driven, the plasticization screw 21 is rotated via a driving transmission mechanism (not shown) arranged in the backflow prevention mechanism 6 and the hopper attachment member 2*a*. The molding material supplied from the hopper 7 to the plasticization cylinder 20 is melted by, for example, the heating of the plasticization cylinder 20 by the heater and the shear heating generated by compression and rotation of the plasticization screw 21. The connection member 5 is heated to the inside of the member by, for example, a heater wound around the outer circumference. The connection member 5 of the preplasticizing injection device using a thermosetting resin material as the molding material may be cooled by a pipe wound around the outer circumference through which a cooling medium flows.

The backflow prevention mechanism 6 is provided to prevent the molding material in the injection chamber 34 from flowing back into the plasticization cylinder 20 when pressure is applied to the inside of the injection chamber 34 by an injection plunger 31 to be described later. As a specific configuration thereof, for example, as shown in US 2018-0133940 A1, it is possible to adopt a configuration in which the plasticization screw 21 is moved forward by the backflow prevention mechanism 6 and the tip of the plasticization screw 21 closes the plasticization part side opening 5*b* of the communication passage 5*a*. Further, the backflow prevention mechanism 6 may also adopt an on-off valve such as a check valve, a rotary valve, or a needle valve which closes the communication passage 5*a* in the middle.

The injection part 3 includes an injection cylinder 30, an injection shaft 31 disposed inside the injection cylinder 30, and an injection nozzle 32 attached to the tip of the injection cylinder 30. An injection hole 32*a*, which communicates with the injection chamber 34 formed inside the injection cylinder 30 and is opened to the outside, is formed in the injection nozzle 32 over the entire length of the injection nozzle 32. An injection hole on-off valve 33 which opens and closes the injection hole 32*a* is provided at a tip part of the injection nozzle 32. The injection hole on-off valve 33 may adopt, for example, a check valve, a rotary valve, a needle valve, or the like. The injection cylinder 30 and the injection nozzle 32 are heated to the inside of the cylinder by, for example, a heater wound around the outer circumference. In addition, the injection part of the preplasticizing injection device using a thermosetting resin material as the molding material may be cooled by, for example, a pipe wound around the outer circumference of the injection cylinder and the injection nozzle through which a cooling medium flows.

The injection shaft 31 is the injection plunger 31 or an injection screw (not shown). Hereinafter, the injection plunger 31 will be described as an example. A gas supply hole 31*a* which extends over the entire length of the injection plunger 31 is provided in a center part of the injection plunger 31, and a spring valve 31*b* capable of opening and closing the gas supply hole 31*a* is accommodated in a tip part (i.e., an end part on the side of the injection nozzle 32) of the gas supply hole 31*a*. The gas supply hole 31*a* guides the gas supplied from the gas supply device 8 into the injection chamber 34.

Figure 2:
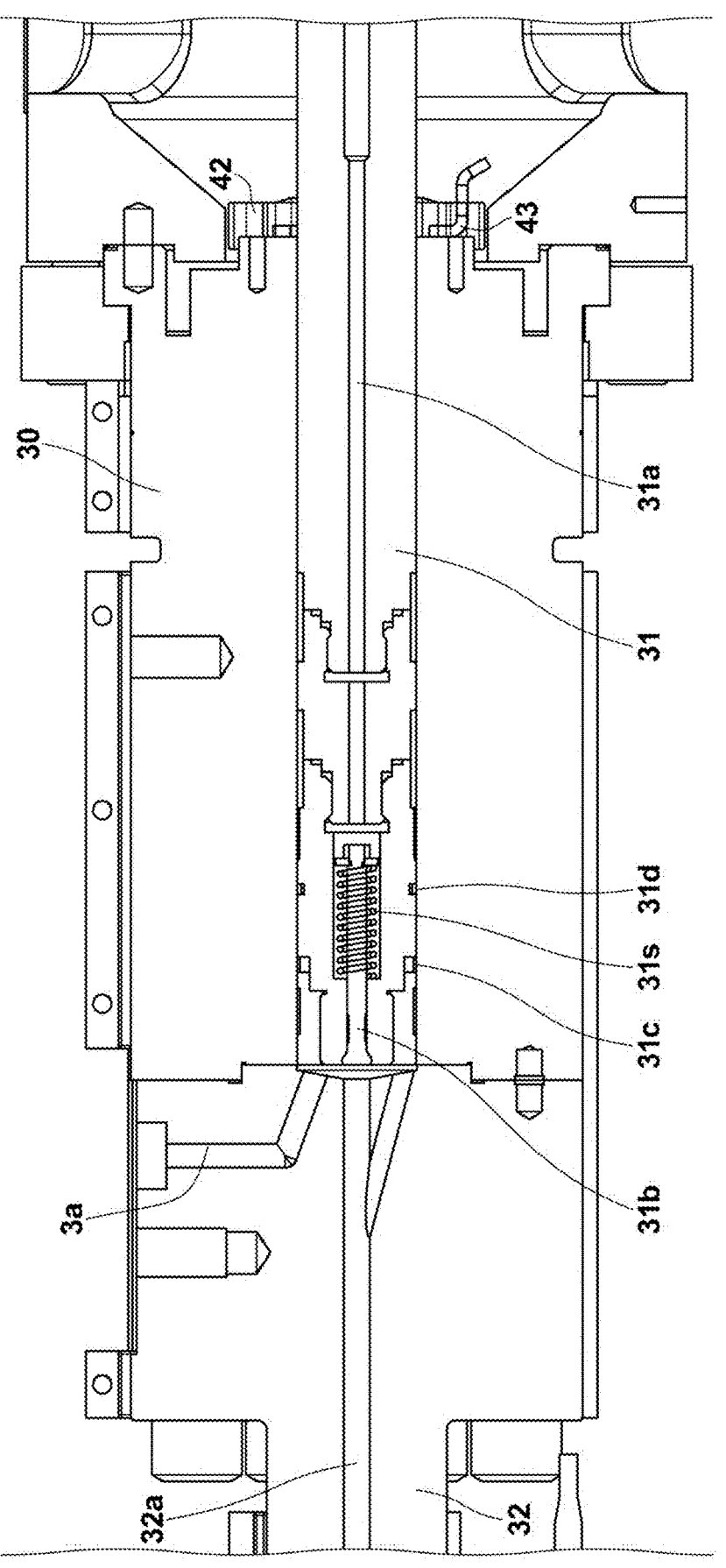
FIG. 2 is an enlarged sectional view showing a part of the gas injection device.

FIG. 1 schematically shows the above-described configuration of the injection part 3. FIG. 2 is a sectional view showing the above configuration in more detail. It is noted that FIG. 2 shows a state in which the injection plunger 31 is positioned as close to the injection nozzle 32 as possible. As shown in FIG. 2, the spring valve 31*b* is biased toward the right in the figure by a coil spring 31*s*, and if no external force is applied, the biasing force keeps the gas supply hole 31*a* closed. Also, as shown in the figure, at least one seal ring 31*c* and at least one piston ring 31*d* are fitted on the outer circumferential surface of the injection plunger 31 having a substantially cylindrical shape to be aligned in the axial direction of the injection plunger 31. With the seal ring 31*c* and the piston ring 31*d* sliding on the inner circumferential surface of the injection cylinder 30, the injection plunger 31 can move relatively in the cylinder axial direction of the injection cylinder 30 while maintaining an airtight state with respect to the injection cylinder 30. The seal ring 31*c* mainly prevents the gas in the injection chamber 34 from leaking between the inner circumferential surface of the injection cylinder 30 and the outer circumferential surface of the injection plunger 31. The piston ring 31d mainly aligns the injection plunger 31 sliding in the injection cylinder 30 and maintains the posture of the injection plunger 31 to smooth the movement of the injection plunger 31, and meanwhile uniforms the gap between the inner circumferential surface of the injection cylinder 30 and the outer circumferential surface of the injection plunger 31, so that the seal ring 31c surely seals all the gaps and prevents the gas in the injection chamber 34 from leaking from the gaps.

Figure 14:
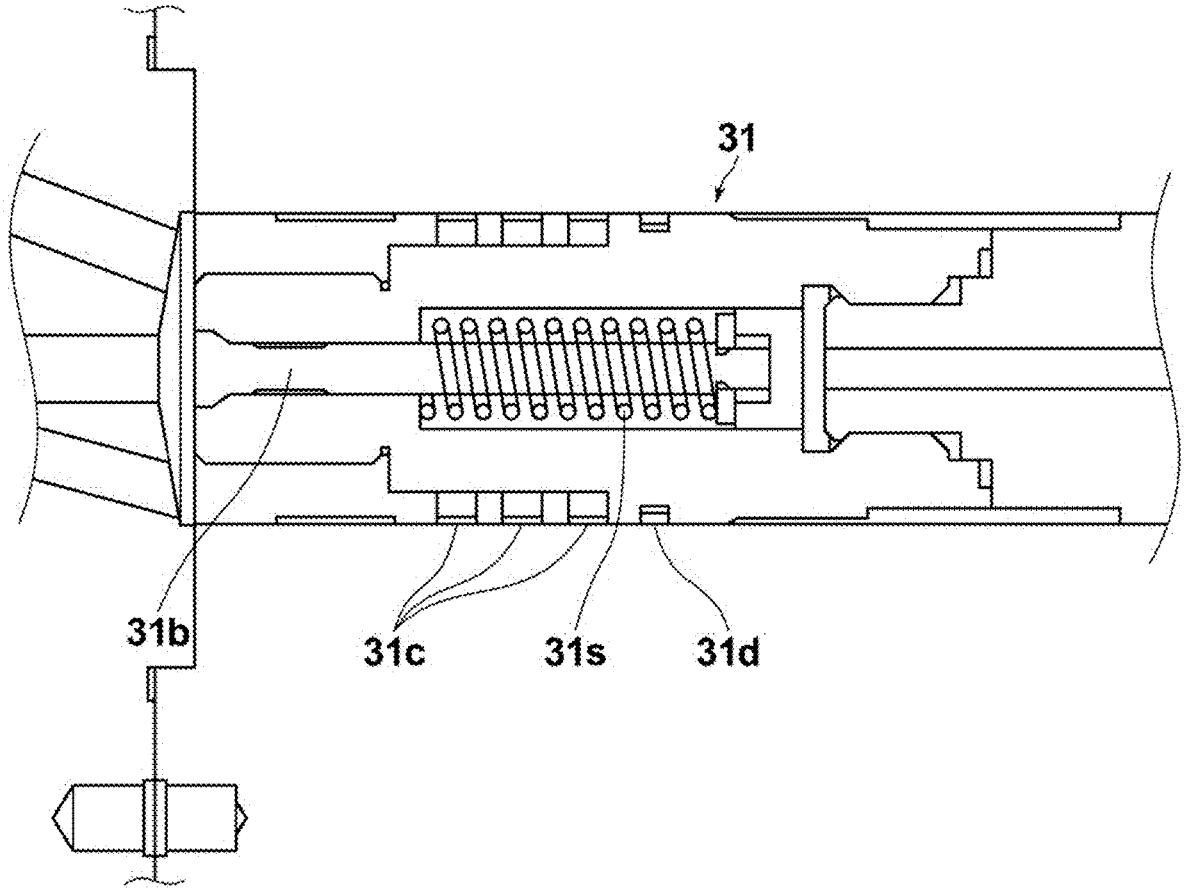
FIG. 14 is a schematic view showing another example of a seal structure between the injection plunger and the injection cylinder.

At least one of the seal rings 31c may be made of metal, for example. Exemplarily, three or more metal seal rings 31c may be fitted on the outer circumferential surface of the injection plunger 31 to be aligned in the axial direction of the injection plunger 31. As a specific example, FIG. 14 shows an example in which three metal seal rings 31c are fitted to be aligned in the axial direction of the injection plunger 31. In FIG. 14, elements equivalent to those in FIG. 2 described above are labeled with the same reference numerals, and descriptions thereof will be omitted unless otherwise necessary (the same applies hereinafter).

Figure 15:
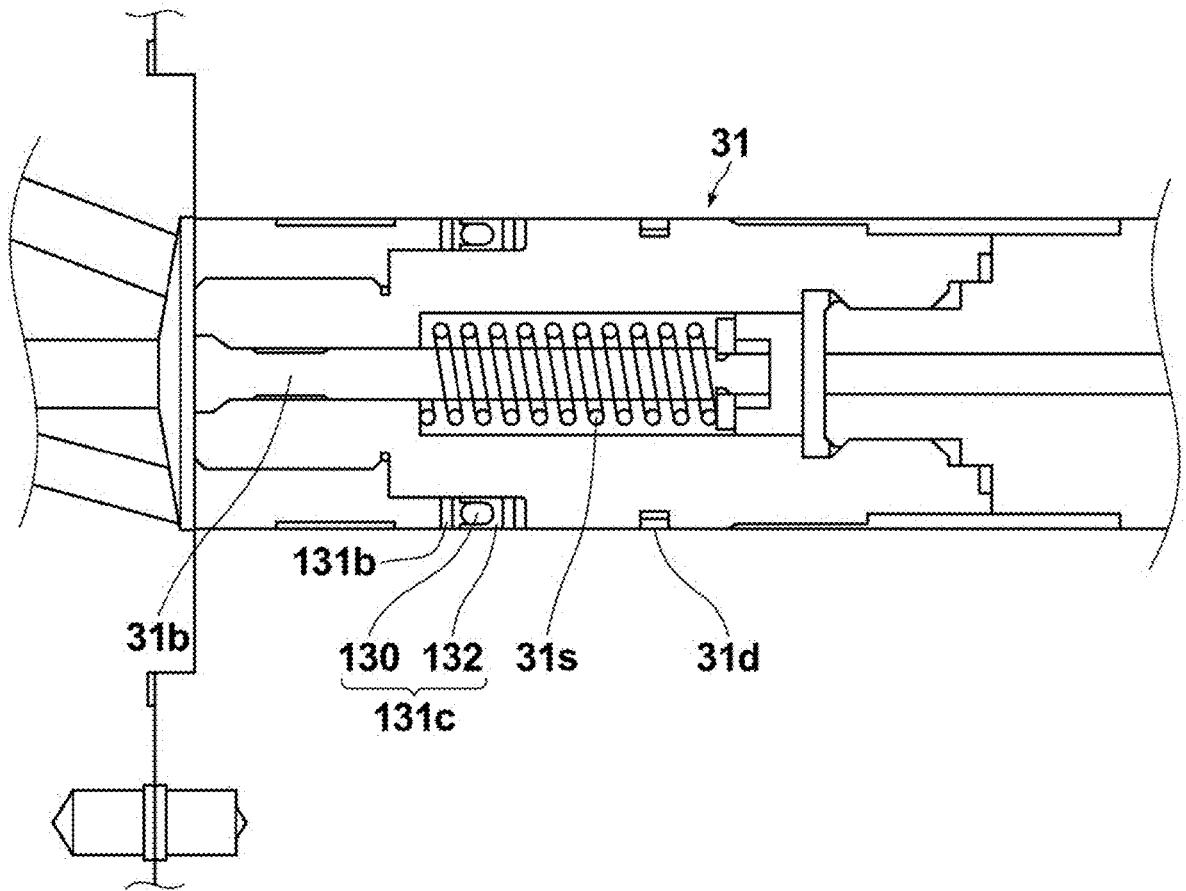
FIG. 15 is a schematic view showing still another example of the seal structure.

At least one of the seal rings 31c may be configured by covering a biasing member with a flexible member, for example. The biasing member is, for example, a spring. The flexible member may have high heat resistance and high abrasion resistance, and may have high sliding properties. The material of the flexible member may include, for example, fluororesin. FIG. 15 shows an example of the seal ring 131c configured by covering a biasing member 130 with a flexible member 132. To prevent the seal ring 131c configured in this manner from being deformed more than necessary and moving from the attachment position, it may be attached to the injection plunger 31 together with a backup ring 131b.

Figure 16:
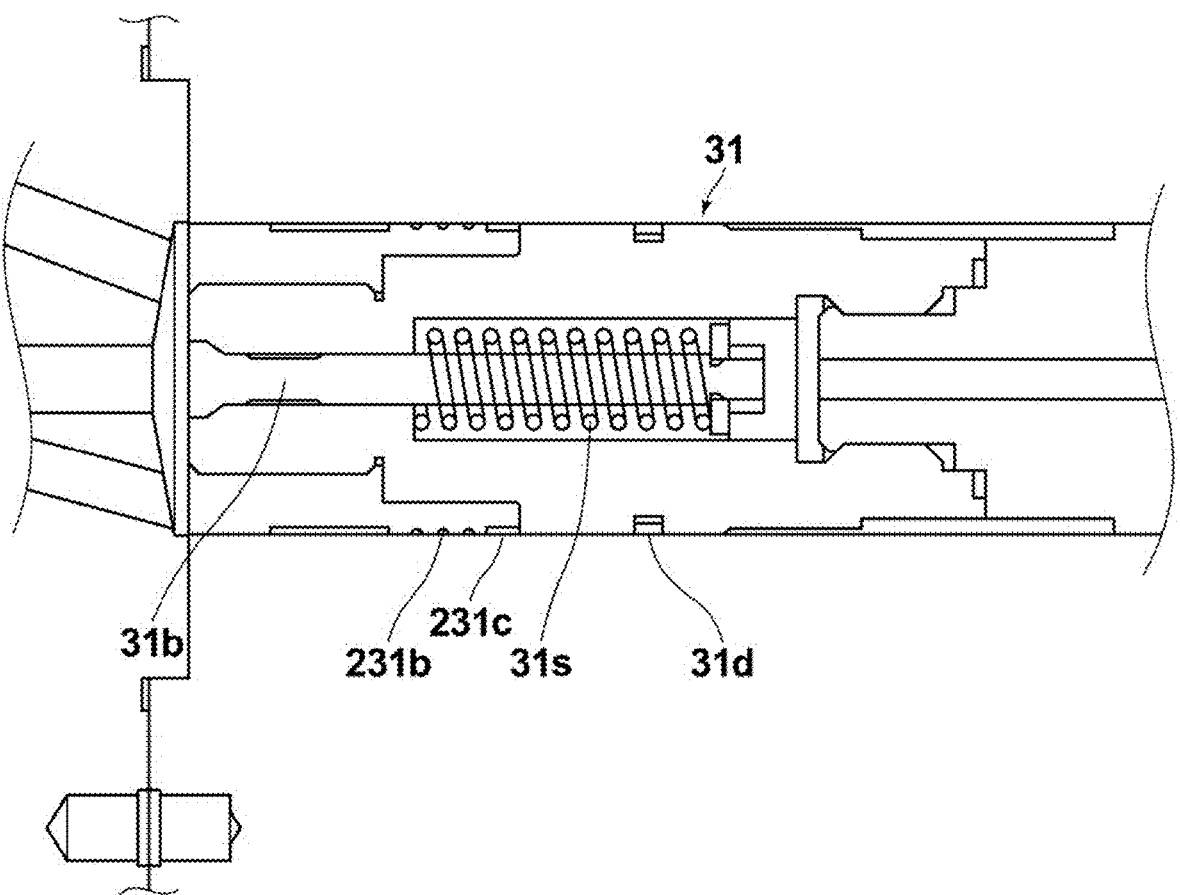
FIG. 16 is a schematic view showing still another example of the seal structure.

Further, as shown in an example in FIG. 16, on the outer circumference of the injection plunger 31, at least one annular groove 231b may be formed on a portion on the forward side of the injection plunger 31 with respect to the seal ring 231c to be aligned with the seal ring 231c in the axial direction of the injection plunger 31.

Hereinafter, returning to FIG. 1 and FIG. 2, the description will be continued. The injection cylinder 30 may include a cooling device 42 at the rear end, as shown in FIG. 2. The cooling device 42 suppresses thermal expansion of a rear end part of the injection cylinder 30 heated by the heater. The gap between the inner circumferential surface of the rear part of the injection cylinder 30 in which thermal expansion is suppressed and the outer circumferential surface of the injection plunger 31 facing the inner circumferential surface of the injection cylinder 30 is suppressed from increasing due to heating of the heater, so that the gas in the injection chamber 34 is prevented from leaking through the gap.

The cooling device 42 may be, for example, a scraper ring provided with a cooling pipe 43 and attached to the rear end part of the injection cylinder 30. The scraper ring provided with the cooling pipe 43 can cool the rear end part of the injection cylinder 30 by a cooling medium supplied from the inlet of the cooling pipe 43 and discharged from the outlet. The scraper ring is a device penetrated by the injection plunger 31 to remove the thin film-shaped molding material attached to the outer circumferential surface of the injection plunger 31. The cooling device 42 may also be a single device other than the scraper ring.

Of the internal space of the injection cylinder 30, the space on the front side of the injection plunger 31, i.e., the space on the side of the injection nozzle 32, is the injection chamber 34 described above. A driving device holding part 35 is provided on the rear side of the injection cylinder 30, i.e., on the right side in FIG. 1, and an injection driving device 36 is held in the driving device holding part 35.

The injection driving device 36 is formed of, for example, a hydraulic-type piston cylinder device or the like and is configured to move a rod 37 in the axial direction of the injection plunger 31. The rod 37 is connected to the injection plunger 31. Therefore, when the rod 37 moves as described above, the injection plunger 31 moves forward and backward. The volume of the injection chamber 34 decreases when the injection plunger 31 moves forward, and increases when the injection plunger 31 moves backward. Herein, the forward movement is a movement to the left in FIG. 1, and the backward movement is a movement to the right in FIG. 1. The position of the injection plunger 31 may be detected by a position detector (not shown) such as a linear encoder or a rotary encoder. The driving of the injection driving device 36 is controlled by an injection control device 38. The injection control device 38 may be included in the above-mentioned control device which controls the entire injection molding machine. The injection control device 38 may control the injection driving device 36 based on the detection value of the position detector. In addition to the hydraulic type, the injection driving device 36 may also be configured as various types such as a pneumatic type or an electric type.

The above-described mold clamping device has a mechanism for opening and closing the mold 4 and has a structure which applies a sufficient pressure (i.e., a mold clamping force) when the mold 4 is filled with the molding material. By applying the mold clamping force, the pressure at the time when the melted resin material enters the mold 4 is not lost, so that the resin material does not come out from the mold 4.

The gas supply device 8 includes, for example, a high-pressure gas cylinder 80 as a gas supply source which stores a gas such as carbon dioxide, a gas passage 81 which sends the gas discharged from the high-pressure gas cylinder 80 into the gas supply hole 31a of the injection plunger 31 via an internal passage (not shown) of the rod 37, and a pressure reducing valve 82, a pressure gauge 83, and a switching valve 84 which are provided on the gas passage 81 sequentially from the side of the high-pressure gas cylinder 80. The gas supply device 8 further includes a branch passage 85 branched from the gas passage 81 on the downstream side of the switching valve 84, i.e., on the side opposite to the high-pressure gas cylinder 80, and a switching valve 86 provided on the branch passage 85. The gas passage 81 forms the gas passage in the disclosure together with the gas supply hole 31a of the injection plunger 31 described above.

In this example, normally, the switching valve 84 is opened and the switching valve 86 is closed so that the gas stored in the high-pressure gas cylinder 80 is sent into the gas supply hole 31a. The pressure of the gas sent into the gas supply hole 31a in this manner may be set to a desired value through the operation of the pressure reducing valve 82. Also, the pressure of the gas may be confirmed by the pressure gauge 83. On the other hand, to maintain and manage the injection part 3, for example, contrary to the above, it is possible to close the switching valve 84 and open the switching valve 86 and discharge to the outside a part of the gas in the gas passage 81 ranging from the gas supply hole 31a to the switching valve 86, so as to reduce the pressure of the gas in the gas passage 81 ranging from the gas supply hole 31a to the switching valve 86 to the atmospheric pressure. Further, the gas supply device 8 may include at least one pressure control valve 92 such as a relief valve at a required position of the gas passage 81 as necessary. It is noted that FIG. 1 shows an example in which two pressure control valves 92 are provided. The pressure control valve 92 discharges the gas to the outside when the pressure of the gas in the gas passage 81 exceeds a predetermined pressure value, so that the pressure of the gas in the gas passage 81 is controlled not to exceed the predetermined pressure value.

The gas supply device 8 further includes, for example, a flow rate sensor 88 provided on the gas passage 81 on the downstream side of the branch passage 85, an integrated flow controller 89 connected to the flow rate sensor 88, and an integrated flow monitor 90 connected to the integrated flow controller 89. The flow rate sensor 88, the integrated flow controller 89, and the integrated flow monitor 90 form a gas integrated flow measuring device 91 which measures the integrated flow of the gas, and the gas integrated flow measuring device 91 is connected to the above-mentioned injection control device 38. For example, a signal indicating the integrated flow of the gas sent into the gas supply hole 31*a* via the gas passage 81 is inputted from the integrated flow monitor 90 to the injection control device 38. The integrated flow controller 89 and the integrated flow monitor 90 may be included in the injection control device 38 or the control device described above. The flow rate sensor 88 may be a mass flow meter. Further, the gas supply device 8 may include a mass flow controller capable of detecting the flow rate of the gas in place of the flow rate sensor 88 and meanwhile controlling the flow rate of the gas. The mass flow controller includes a flow rate sensor, a flow rate control valve, and a control part which controls the flow rate control valve based on the output of the flow rate sensor. The gas supply device 8 may supply the gas at a desired constant flow rate by the mass flow controller. It is noted that some among the mass flow meters have the function of the integrated flow controller 89. Some among the mass flow meters have the function of the integrated flow monitor 90. Some among the mass flow controllers have the function of the integrated flow controller 89. Some among the mass flow controllers have the function of the integrated flow monitor 90. The integrated flow controller 89 may also utilize the function of the integrated flow controller 89 included in the mass flow meter or the mass flow controller. The integrated flow monitor 90 may also utilize the function of the integrated flow monitor 90 included in the mass flow meter or the mass flow controller.

Hereinafter, the operation of the injection device 1 will be described with reference to FIG. 3 to FIG. 13. Generally, in injection molding, the processes of mold closing and mold clamping, injection, pressure holding, cooling, measuring, mold opening, and take-out are sequentially performed, and a molded product is obtained by repeating this molding cycle. FIG. 3 to FIG. 13 schematically show the states of the injection plunger 31, the spring valve 31*b*, and the injection hole on-off valve 33 over time from the time when the above pressure holding is completed for molding one product, until the pressure holding is performed for molding a next product. While the elements in the figures are all labeled in FIG. 3, in FIG. 4 to FIG. 13, only elements requiring description are labeled in order to avoid complication of the figures.

Also, the forward and backward positions of the injection plunger 31 inside the injection cylinder 30 are determined by the operation of the injection driving device 36 controlled by the injection control device 38 as described above. However, in the following description, unless otherwise necessary, the control of the injection control device 38 and the operation of the injection driving device 36 will not be described one by one, but only the operation or position of the injection plunger 31 may be described.

Figure 3:
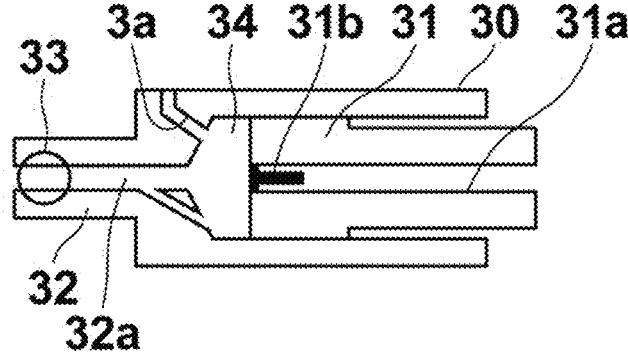
FIG. 3 is a schematic view showing a state in which a previous pressure holding process is completed.

First, the position of the injection plunger 31 is in a state shown in FIG. 3 at the time when the pressure holding process is completed. Further, the injection hole on-off valve 33 is in a state of opening the injection hole 32*a* of the injection nozzle 32. At this time, the molding material remains in the injection chamber 34 in front of the injection plunger 31. Also, at this time, the back flow prevention mechanism 6 closes the communication passage 5*a*. The operation of the backflow prevention mechanism 6 is controlled by, for example, the injection control device 38 but is not limited thereto, and may also be controlled by the control device which controls the operation of the entire injection molding machine.

Figure 4:
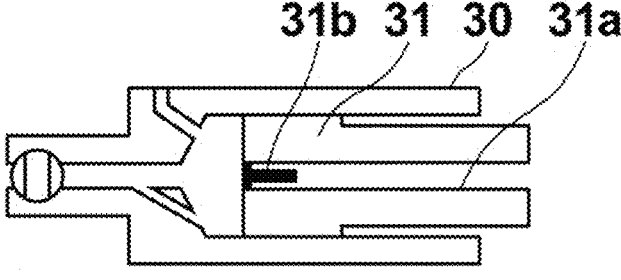
FIG. 4 is a schematic view showing a state in which an injection hole of an injection nozzle is closed.

From the above state, next, as shown in FIG. 4, the injection hole on-off valve 33 formed by, for example, a solenoid valve is changed to a state of closing the injection hole 32*a* of the injection nozzle 32. The operation of the injection hole on-off valve 33 is controlled by, for example, the injection control device 38 but is not limited thereto, and may also be controlled by the control device which controls the operation of the entire injection molding machine. After the injection hole on-off valve 33 is changed to the above state, a mold opening process of opening the mold 4 by the mold clamping device and a take-out process of taking out the cooled molded product from the opened mold 4 are performed.

Figure 5:
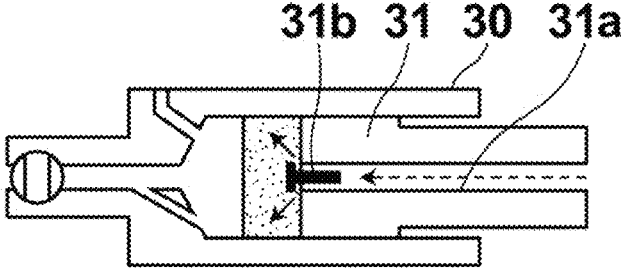
FIG. 5 is a schematic view showing a state in which an injection plunger moves backward to a predetermined position while feeding a gas into an injection chamber via a gas supply hole.

Next, as shown in FIG. 5, the injection plunger 31 is moved backward to a predetermined position at a predetermined speed while feeding the gas into the gas supply hole 31*a* via the gas passage 81 shown in FIG. 1. The gas pressure at this time is set to, for example, about 5 MPa or less by the pressure reducing valve 82 shown in FIG. 1. Due to the pressure of this gas and the negative pressure caused by the backward movement of the injection plunger 31, the spring valve 31*b* opens the gas supply hole 31*a* against the biasing force of the coil spring 31*s*. As a result, the gas is sent from the gas supply hole 31*a* to the internal space (i.e., the injection chamber 34) of the injection cylinder 30. Since this gas is not so high in pressure as above, it is basically prevented from dissolving in the molding material remaining in the injection chamber 34.

Figure 6:
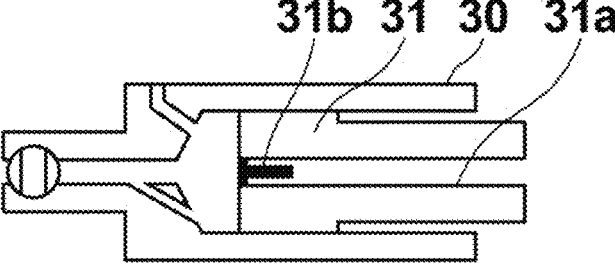
FIG. 6 is a schematic view showing a state in which the injection plunger moves forward and the gas in the injection chamber is compressed and dissolved in the molding material in the injection chamber.

Next, as shown in FIG. 6, the injection plunger 31 is moved forward at a predetermined pressure for a predetermined time. Thereby, the gas sent to the injection chamber 34 is compressed and dissolved in the molding material remaining in the injection chamber 34. As the spring valve 31*b* has the configuration shown in FIG. 2, it is possible to prevent the gas sent to the injection chamber 34 from flowing back to the gas supply hole 31*a*. When the pressure which is the sum of the gas pressure in the injection chamber and the biasing force of the coil spring 31*s* becomes larger than the gas pressure in the gas supply hole 31*a*, the spring valve 31*b* closes the gas supply hole 31*a*.

Figure 7:
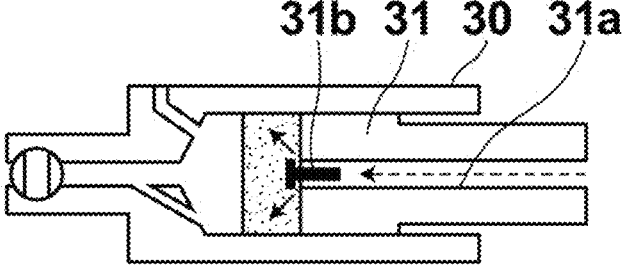
FIG. 7 is a schematic view showing a state in which the injection plunger moves backward to a predetermined position while feeding the gas into the injection chamber via the gas supply hole.

Next, as shown in FIG. 7, in the same manner as shown in FIG. 5, the injection plunger 31 is moved backward to a predetermined position at a predetermined speed. Thereby, the gas is sent from the gas supply hole 31*a* to the injection chamber 34 of the injection cylinder 30. Also, in this case, the gas is basically prevented from dissolving in the molding material remaining in the injection chamber 34.

Figure 8:
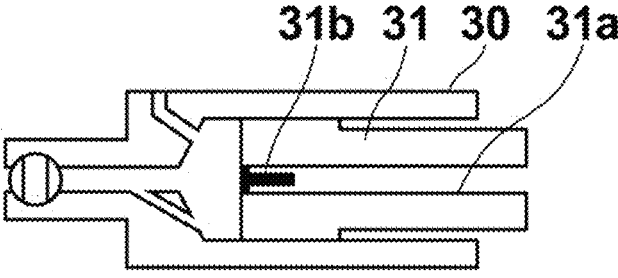
FIG. 8 is a schematic view showing a state in which the injection plunger moves forward and the gas in the injection chamber is compressed and dissolved in the molding material in the injection chamber.

Next, as shown in FIG. 8, in the same manner as shown in FIG. 6, the injection plunger 31 is moved forward at a predetermined pressure for a predetermined time Thereby, the gas sent to the injection chamber 34 is compressed and dissolved in the molding material remaining in the injection chamber 34.

Figure 9:
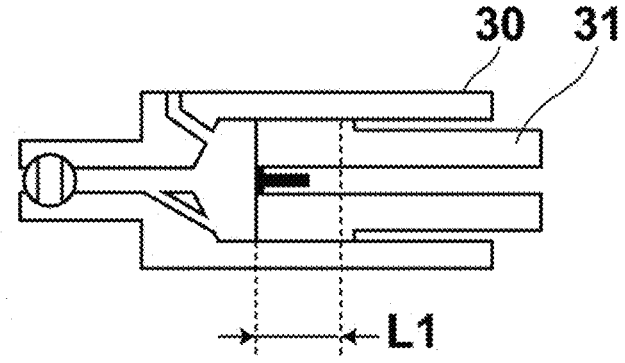
FIG. 9 is a schematic view showing a state in which a predetermined amount of the gas is compressed and dissolved in the molding material in the injection chamber, and afterwards the injection plunger is returned to a position at the time when the previous pressure holding process was completed.

As described above, the backward movement and the forward movement of the injection plunger 31 are repeated for a plurality of cycles. Meanwhile, the flow rate sensor 88 shown in FIG. 1 detects the flow rate of the gas flowing through the gas passage 81, and the integrated flow controller 89 calculates the integrated flow based on the flow rate of the gas. Then, the integrated flow is monitored by the integrated flow monitor 90, and a signal indicating the integrated flow is inputted to the injection control device 38. When the integrated flow indicated by this signal reaches a target value (e.g., a desired amount to be supplied into the injection chamber 34), the injection control device 38 controls the operation of the injection driving device 36 to return the position of the injection plunger 31 to the position at the time when the initial pressure holding process was completed. FIG. 9 shows the state at this time. When the integrated flow reaches a predetermined target value, the integrated flow monitor 90 may output a signal indicating this to the injection control device 38. When a signal indicating that the integrated flow has reached the predetermined target value is inputted, the injection control device 38 may control the operation of the injection driving device 36 to return the position of the injection plunger 31 to the position at the time when the initial pressure holding process was completed. The injection control device 38 may include the integrated flow monitor 90 and may be inputted with a signal indicating the integrated flow calculated by the integrated flow controller 89. When the integrated flow reaches the predetermined target value, the injection control device 38 may control the operation of the injection driving device 36 to return the position of the injection plunger 31 to the position at the time when the initial pressure holding process was completed. The injection control device 38 may include the integrated flow controller 89 and the integrated flow monitor 90 and may be inputted with a signal indicating the flow rate of the gas detected by the flow rate sensor 88. An integrated flow is calculated based on the flow rate of the gas, and when the integrated flow reaches the predetermined target value, the injection control device 38 may control the operation of the injection driving device 36 to return the position of the injection plunger 31 to the position at the time when the initial pressure holding process was completed.

Next, the injection control device 38 opens the communication passage 5a and applies a predetermined back pressure to the injection plunger 31 by the injection driving device 36, and meanwhile drives the rotation driving device 22 of FIG. 1 to rotate the plasticization screw 21 and supplies the molten molding material from the hopper 7 into the plasticization cylinder 20. In addition to directly controlling the driving of the rotation driving device 22 by the injection control device 38 in the above manner, a dedicated rotation driving control part which controls the driving of the rotation driving device 22 may also be provided, and the rotation driving control part may be controlled by the injection control device 38. The molding material supplied into the plasticization cylinder 20 is kneaded and meanwhile sent to the front, i.e., toward the communication passage 5a, by the rotating plasticization screw 21. The molding material sent from the plasticization part side opening 5b of the connection member 5 into the communication passage 5a passes through the communication passage 3a and is sent to the injection chamber 34 of the injection part 3.

Figure 10:
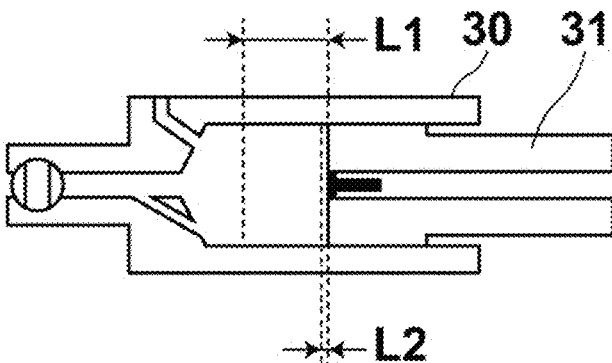
FIG. 10 is a schematic view showing a state in which a measuring process is completed.

FIG. 10 shows the state at this time, and as shown in the figure, the injection plunger 31 is pushed back by the molding material supplied to the injection chamber 34. In the injection chamber 34, by mixing the molding material in which the gas has already been compressed and dissolved with the molding material newly supplied to the injection chamber 34, the gas supplied to the injection chamber 34 is compressed and dissolved under high pressure. The injection control device 38 shown in FIG. 1 stops the injection plunger 31 at the position where the measuring is completed, i.e., the position where the measured amount of the molding material reaches a predetermined amount. Reference numeral L1 in FIG. 9 and FIG. 10 indicates the retracted length of the injection plunger 31 from the position of FIG. 9 to the stop position.

Figure 11:
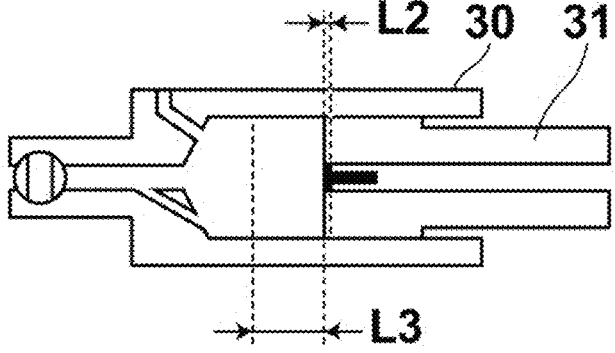
FIG. 11 is a schematic view showing a state in which the injection plunger moves forward to promote compression and dissolution of the gas into the molding material in the injection chamber, while maintaining a state in which the gas is compressed and dissolved in the molding material in the injection chamber.

After the above measuring is completed and the backflow prevention mechanism 6 closes the communication passage 5a, the injection control device 38 moves the injection plunger 31 forward at a predetermined pressure until the process of injecting the molding material into the mold 4 is started. FIG. 11 shows the state after this forward movement has been performed. Reference numeral L2 in FIG. 10 and FIG. 11 indicates the length of this forward movement. By moving the injection plunger 31 forward in this manner, the molding material and the gas are further compressed, the dissolution of the gas in the molding material is promoted, and the state in which the gas is compressed and dissolved in the molding material is maintained. Therefore, the molding material is dissolved with the gas, so that the viscosity is lowered and the plasticity is increased.

Next, the injection control device 38 corrects the position of the injection plunger 31 at the time of completion of measuring the molding material, which is stored in, for example, an internal memory, as the position after the above forward movement is performed. The position of the injection plunger 31 at the time of completion of measuring the molding material is the position where the injection plunger 31 starts to move forward when the molding material is injected into the mold 4.

Figure 12:
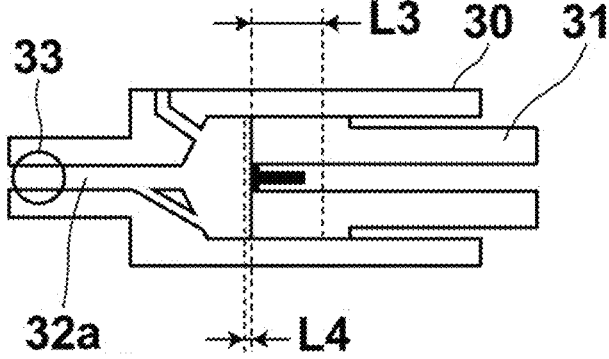
FIG. 12 is a schematic view showing a state in which the injection hole of the injection nozzle is opened and a state in which an injection process is completed.

Next, after the injection hole on-off valve 33 is changed to a state of opening the injection hole 32a of the injection nozzle 32, the injection control device 38 moves the injection plunger 31 forward at a predetermined speed for a predetermined distance as shown in FIG. 12. Reference numeral L3 in FIG. 11 and FIG. 12 indicates the length of this forward movement. By moving the injection plunger 31 forward in this manner, the molding material in which the gas is dissolved and the viscosity is lowered is injected into the mold 4 via the injection hole 32a of the injection nozzle 32.

Figure 13:
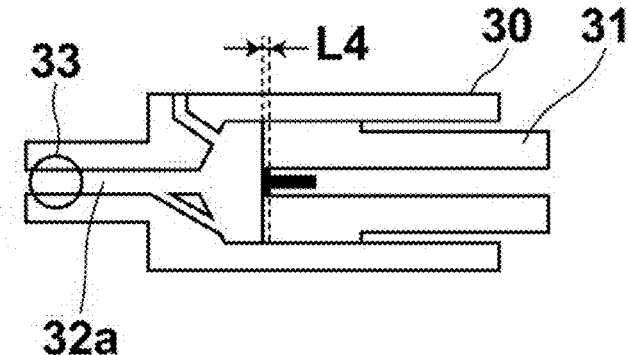
FIG. 13 is a schematic view showing a state in which the pressure holding process is completed.

Then, as shown in FIG. 13, the injection control device 38 performs pressure holding which moves the injection plunger 31 forward at a predetermined pressure for a predetermined time, until the molding material of a gate portion in the mold 4 is cooled and solidified. Reference numeral LA in FIG. 12 and FIG. 13 indicates the length of the forward movement of the injection plunger 31 at this time.

The injection control device 38 or the control device described above may control the injection device 1 according to the gas dissolution method of the injection device which can realize the injection device 1 of the disclosure. The injection control device 38 or the control device described above may control the injection device 1 according to a program read, by using a reading device (not shown), from a storage medium 39 storing the program of the injection device which can realize the injection device 1 of the disclosure.

In the present embodiment, the gas supply hole 31a penetrates the injection plunger 31. The gas supply hole 31a is opened at the tip surface of the injection plunger 31 and, when the injection plunger 31 moves backward, communicates with the space in the injection chamber 34 between the tip surface of the injection plunger 31 and the molding material in the injection chamber 34. In the space communicating with the gas supply hole 31a, the pressure in the space is lowered due to the negative pressure resulting from the volume expansion by moving the injection plunger 31 backward. The gas is supplied into the injection chamber 34 from the opening of the gas supply hole 31a as the pressure in the space becomes smaller than the pressure in the gas supply hole 31a due to the negative pressure.

Generally, the molding material remains in the injection nozzle 32 and the injection chamber 34 after the pressure holding process. For example, when the gas supply hole 31a is opened in the injection nozzle 32, or when the gas supply hole 31a is opened to the wall surface of the injection chamber 34 facing the tip surface of the injection plunger 31, the gas temporarily pushes away the molding material which covers the opening of the gas supply hole 31a, and reaches the space where the internal pressure is lowered by the negative pressure.

The flow rate of the gas flowing from the gas supply hole 31a into the space in which the internal pressure is lowered by the negative pressure decreases as the pressure difference between the pressure in the space where the internal pressure is lowered by the negative pressure and the pressure in the gas supply hole 31a decreases, and it is possible that the molding material covering the opening of the gas supply hole 31a cannot be pushed away. Further, the molding material covering at least a part of the opening of the gas supply hole 31a may cause the gas supply from the gas supply hole 31a to be stopped halfway.

The amount of the molding material remaining in the injection chamber 34 after the pressure holding process varies depending on the molding cycle. The amount of the molding material covering the opening of the gas supply hole 31a after the pressure holding process varies depending on the molding cycle. For the above reason, the timing at which the gas supply is stopped may vary depending on the molding cycle. Since the timing at which the gas supply is stopped varies, the supply amount of the gas supplied into the injection chamber 34 may vary depending on the molding cycle.

In the present embodiment, since the opening of the gas supply hole 31a is provided in the tip surface of the injection plunger 31, and the injection plunger 31 is moved backward when the gas is supplied, at least part of the opening of the gas supply hole 31a is not covered with the molding material during the gas supply. In the present embodiment, a predetermined amount of gas can be accurately supplied into the injection chamber 34 for each molding cycle, and the gas supply amount can be correctly controlled.

In the present embodiment, a space is formed in front of the opening of the gas supply hole 31a immediately after the injection plunger 31 starts to move backward. In the present embodiment, even immediately after the injection plunger 31 starts to move backward, the gas supply can be started as long as the above-mentioned pressure difference exists, so the stroke in which the injection plunger 31 moves backward can be shortened.

In the present embodiment, to compress and dissolve a predetermined amount of gas in the molding material in the injection chamber 34, the injection plunger 31 is moved backward and forward for a plurality of cycles.

Generally, the molding material remains in the injection nozzle 32 and the injection chamber 34 after the pressure holding process. In the pressure holding process, after injecting the molding material into the mold, a predetermined holding pressure is applied by the injection plunger 31 to the molding material in the mold through the molding material remaining in the injection chamber 34 and the molding material remaining in the injection nozzle 32. At this time, the molding material in the injection chamber 34 contracts according to the elasticity of the molding material. When the pressure holding process is completed, the holding pressure is not applied by the injection plunger 31. The molding material which has contracted in the injection chamber 34 generates a repulsive force for returning to its original state. When the pressure holding process is completed, the injection plunger 31 is pushed back in the backward direction by the repulsive force due to the elasticity of the molding material.

The amount of the molding material remaining in the injection chamber 34 after the pressure holding process varies depending on the molding cycle. The stroke of the injection plunger 31 moving in the backward direction due to the repulsion of the molding material after the pressure holding process varies depending on the molding cycle. Due to these variations, the pressure in the injection chamber 34 before the negative pressure is generated may vary depending on the molding cycle. Afterwards, when the injection plunger 31 is moved backward, the pressure in the injection chamber 34, in which the internal pressure is lowered due to the negative pressure, may also vary depending on the molding cycle. As described above, the gas is supplied into the injection chamber 34 via the opening of the gas supply hole 31a due to the pressure difference. When the injection plunger 31 is moved backward only once and a predetermined amount of gas is supplied once into the injection chamber 34, the gas supply amount may vary depending on the molding cycle.

In the present embodiment, after supplying an amount of gas less than a predetermined amount of gas into the injection chamber 34, by repeatedly compressing and dissolving the gas in the molding material in the injection chamber 34 until the predetermined amount of gas is supplied into the injection chamber 34, the predetermined amount of gas can be accurately supplied into the injection chamber 34 for each molding cycle, and the gas supply amount can be correctly controlled.

In the present embodiment, the stroke of the reciprocating movement of the injection plunger 31 may be set to be shorter than in the case where the injection plunger 31 is moved backward and forward only once.

Generally, to set the stroke of the reciprocating movement of the injection plunger 31 to be longer, it is necessary to form the injection cylinder 30 to have a greater total length. If the total length of the injection cylinder 30 is greater, the injection plunger 31 is separated from the plasticization cylinder 20 and the injection chamber 34 and also passes through a part of the injection cylinder 30 which has a low temperature. In such a case, the molding material in a molten state which is adhered to the injection plunger 31 in the injection chamber 34 may be cooled and thinly solidified.

If this solidified molding material remains unevenly on the inner circumferential surface of the injection cylinder 30, the gap between the inner circumferential surface of the injection cylinder 30 and the outer circumferential surface of the injection plunger 31 becomes uneven. The uneven gap may not be able to be sealed by the seal ring 31c attached to the injection plunger 31 and may cause the gas in the injection chamber 34 to leak. If the stroke of the reciprocating movement of the injection plunger 31 is set to be longer, the gas supply amount may not be correctly controlled. On the other hand, if the stroke of the reciprocating movement of the injection plunger 31 can be set to be shorter, the above issues can be avoided and the gas supply amount can be correctly controlled.

The injection device of the disclosure is not limited to the above-described embodiment and may be appropriately changed without departing from the spirit of the disclosure.

What is claimed is:

1. An injection device which injects a molding material into a mold, the injection device comprising:

an injection cylinder formed with an injection chamber accommodating the molding material;

a supply device supplying the molding material into the injection chamber;

a gas supply device supplying a gas into the injection chamber to compress and dissolve the gas in the molding material supplied into the injection chamber;

a gas integrated flow measuring device measuring an integrated flow of the gas supplied into the injection chamber;

an injection shaft reciprocating in a cylinder axis direction in the injection chamber and formed with a gas supply hole penetrating inside the injection shaft, wherein one end part of the gas supply hole is opened on a tip surface forming a part of a wall surface of the injection chamber, and another end part of the gas supply hole is connected to the gas supply device to guide the gas from the gas supply device into the injection chamber;

an injection driving device causing the injection shaft to reciprocate in the cylinder axis direction; and an injection control device configured to control the injection driving device to move the injection shaft backward and forward in the injection chamber to expand and reduce the injection chamber before supplying the molding material from the supply device into the injection chamber, such that when compressing and dissolving a predetermined amount of the gas in the molding material remaining in the injection chamber, a cycle from moving the injection shaft backward to supply the gas into the injection chamber to moving the injection shaft forward to compress and dissolve the gas in the injection chamber into the molding material in the injection chamber is performed for at least one time until the integrated flow measured by the gas integrated flow measuring device reaches the predetermined amount, wherein the injection control device is configured to stop backward movement of the injection shaft and move the injection shaft forward to an initial position when the integrated flow measured by the gas integrated flow measuring device reaches the predetermined amount, and then, as the injection shaft is pushed back by the molding material supplied into the injection chamber from the supply device, stop the injection shaft at a position where an amount of the molding material in the injection chamber reaches a predetermined amount, thereafter move the injection shaft forward at a predetermined speed for a predetermined distance to inject the molding material into the mold, and thereafter to perform a pressure holding process in which the injection driving device moves the injection shaft forward at the predetermined pressure for a predetermined time, wherein the initial position is a position at a time when a previous pressure holding process was completed.

2. The injection device according to claim 1, wherein the gas supply device is composed of a high-pressure gas cylinder and a pressure reducing valve to supply into the injection chamber a gas of pressure lower than a pressure capable of dissolving in the molding material.

3. The injection device according to claim 1, further comprising a valve which opens an opening of the one end part of the gas supply hole when the injection shaft moves backward, and closes the opening of the one end part of the gas supply hole when the injection shaft moves forward.

4. The injection device according to claim 2, further comprising a valve which opens an opening of the one end part of the gas supply hole when the injection shaft moves backward, and closes the opening of the one end part of the gas supply hole when the injection shaft moves forward.

5. The injection device according to claim 1, wherein the injection shaft is an injection plunger.

6. An injection device which injects a molding material into a mold, the injection device comprising:

an injection cylinder formed with an injection chamber accommodating the molding material;

a supply device supplying the molding material into the injection chamber;

a gas supply device supplying a gas into the injection chamber to compress and dissolve the gas in the molding material supplied into the injection chamber;

a gas integrated flow measuring device measuring an integrated flow of the gas supplied into the injection chamber;

an injection shaft reciprocating in a cylinder axis direction in the injection chamber;

an injection driving device causing the injection shaft to reciprocate in the cylinder axis direction; and an injection control device configured to control the injection driving device to move the injection shaft backward and forward in the injection chamber to expand and reduce the injection chamber before supplying the molding material from the supply device into the injection chamber, such that when compressing and dissolving a predetermined amount of the gas in the molding material remaining in the injection chamber, a cycle from moving the injection shaft backward to supply the gas into the injection chamber to moving the injection shaft forward to compress and dissolve the gas in the injection chamber into the molding material in the injection chamber is performed for at least one time until the integrated flow measured by the gas integrated flow measuring device reaches the predetermined amount, wherein the injection control device is configured to stop backward movement of the injection shaft and move the injection shaft forward to an initial position when the integrated flow measured by the gas integrated flow measuring device reaches the predetermined amount, and then, as the injection shaft is pushed back by the molding material supplied into the injection chamber from the supply device, stop the injection shaft at a position where an amount of the molding material in the injection chamber reaches a predetermined amount, thereafter move the injection shaft forward at a predetermined speed for a predetermined distance to inject the molding material into the mold, and thereafter to perform a pressure holding process in which the injection driving device moves the injection shaft forward at the predetermined pressure for a predetermined time, wherein the initial position is a position at a time when a previous pressure holding process was completed.

7. The injection device according to claim 6, wherein the gas supply device is composed of a high-pressure gas cylinder and a pressure reducing valve to supply into the injection chamber a gas of pressure lower than a pressure capable of dissolving in the molding material.

8. The injection device according to claim 6, wherein at least one of the seal rings is made of metal.

9. The injection device according to claim 7, wherein at least one of the seal rings is made of metal.

10. The injection device according to claim 6, wherein at least one of the seal rings is configured by a biasing member and a flexible member covering the biasing member.

11. The injection device according to claim 7, wherein at least one of the seal rings is configured by a biasing member and a flexible member covering the biasing member.

12. The injection device according to claim 6, wherein on the outer circumferential surface of the injection shaft, the injection shaft is formed with at least one annular groove on a portion on a forward side of the injection shaft with respect to the seal ring to be aligned with the seal ring in an axial direction.

13. The injection device according to claim 7, wherein on the outer circumferential surface of the injection shaft, the injection shaft is formed with at least one annular groove on a portion on a forward side of the injection shaft with respect to the seal ring to be aligned with the seal ring in an axial direction.

14. The injection device according to claim 6, wherein the injection cylinder comprises a cooling device at a rear end part.

15. The injection device according to claim 7, wherein the injection cylinder comprises a cooling device at a rear end part.

16. The injection device according to claim 6, wherein the injection shaft is an injection plunger.

17. The injection device according to claim 6, wherein the injection shaft is configured to reciprocate in the cylinder axis direction in the injection chamber and is formed with a gas supply hole penetrating inside the injection shaft, wherein one end part of the gas supply hole is opened on a tip surface forming a part of a wall surface of the injection chamber, and another end part of the gas supply hole is connected to the gas supply device to guide the gas from the gas supply device into the injection chamber.

18. The injection device according to claim 17, further comprising a valve which opens an opening of the one end part of the gas supply hole when the injection shaft moves backward, and closes the opening of the one end part of the gas supply hole when the injection shaft moves forward.

19. The injection device according to claim 7, wherein the injection shaft is configured to reciprocate in the cylinder axis direction in the injection chamber and is formed with a gas supply hole penetrating inside the injection shaft, wherein one end part of the gas supply hole is opened on a tip surface forming a part of a wall surface of the injection chamber, and another end part of the gas supply hole is connected to the gas supply device to guide the gas from the gas supply device into the injection chamber.

20. The injection device according to claim 19, further comprising a valve which opens an opening of the one end part of the gas supply hole when the injection shaft moves backward, and closes the opening of the one end part of the gas supply hole when the injection shaft moves forward.

* * * * *